United States Patent
Fouts et al.

(10) Patent No.: US 12,412,407 B2
(45) Date of Patent: Sep. 9, 2025

(54) SYSTEMS AND METHODS FOR CLASSIFYING AND ANNOTATING IMAGES TAKEN DURING A MEDICAL PROCEDURE

(71) Applicant: Stryker Corporation, Kalamazoo, MI (US)

(72) Inventors: Brian Fouts, Morgan Hill, CA (US); Cole Kincaid Hunter, Santa Clara, CA (US); Harmandip Singh Sodhi, San Jose, CA (US)

(73) Assignee: Stryker Corporation, Portage, MI (US)

( * ) Notice: Subject to any disclaimer, the term of this patent is extended or adjusted under 35 U.S.C. 154(b) by 648 days.

(21) Appl. No.: 17/565,389

(22) Filed: Dec. 29, 2021

(65) Prior Publication Data

US 2022/0207896 A1    Jun. 30, 2022

Related U.S. Application Data

(60) Provisional application No. 63/132,445, filed on Dec. 30, 2020.

(51) Int. Cl.
*G06V 20/70* (2022.01)
*G06F 18/214* (2023.01)
(Continued)

(52) U.S. Cl.
CPC ............ *G06V 20/70* (2022.01); *G06F 18/214* (2023.01); *G06N 20/00* (2019.01); *G06T 7/0012* (2013.01);
(Continued)

(58) Field of Classification Search
CPC ...... G06V 20/70; G06V 20/41; G06V 10/764; G06V 2201/03; G16H 30/40; G06N 20/00;
(Continued)

(56) References Cited

U.S. PATENT DOCUMENTS 8,443,279 B1   5/2013 Hameed
9,075,899 B1 * 7/2015 Reicher ................. G16H 30/20
(Continued)

FOREIGN PATENT DOCUMENTS

WO   2020/023740 A1   1/2020
WO   2020/056086 A1   3/2020

OTHER PUBLICATIONS

Vasilakakis, Michael D., et al. "Weakly supervised multilabel classification for semantic interpretation of endoscopy video frames." Evolving Systems 11.3 (2020): 409-421. (Year: 2020).*

(Continued)

*Primary Examiner* — Jonathan S Lee
(74) *Attorney, Agent, or Firm* — Morrison & Foerster LLP

(57) ABSTRACT

A method for automatically generating and applying annotations to one or more images captured during a surgical procedure using an imaging tool are provided. In one or more examples, the annotations can be generated by applying one or more machine learning classifiers to the images to determine the presence of various features contained within the images. Optionally, the machine learning classifiers can be configured to determine the anatomy displayed in a particular image as well as the procedure step shown in a given image. Using these two determinations, the systems and methods described herein can generate one or more annotations that are then overlaid on or laid next to an image so as to provide the patient or other person viewing the image with context as to what the image is showing.

24 Claims, 11 Drawing Sheets

(51) Int. Cl.
*G06N 20/00* (2019.01)
*G06T 7/00* (2017.01)
*G06V 10/764* (2022.01)
*G06V 20/40* (2022.01)
*G16H 30/40* (2018.01)

(52) U.S. Cl.
CPC ............ *G06V 10/764* (2022.01); *G06V 20/41* (2022.01); *G16H 30/40* (2018.01); *G06T 2207/10016* (2013.01); *G06T 2207/20081* (2013.01); *G06T 2207/30004* (2013.01); *G06T 2207/30168* (2013.01); *G06V 2201/03* (2022.01)

(58) Field of Classification Search
CPC ................. G06F 18/214; G06T 7/0012; G06T 2207/10016; G06T 2207/20081; G06T 2207/30004; G06T 2207/30168
USPC .......................................................... 382/167
See application file for complete search history.

(56) References Cited

U.S. PATENT DOCUMENTS

| | | |
|---|---|---|
| 2016/0100909 A1 | 4/2016 | Wollowick |
| 2016/0103810 A1 | 4/2016 | Hanning |
| 2019/0069957 A1 | 3/2019 | Barral |
| 2019/0362834 A1 | 11/2019 | Venkataraman et al. |
| 2020/0027210 A1 | 1/2020 | Haemel |
| 2023/0245753 A1 | 8/2023 | Kumar |

OTHER PUBLICATIONS

Palmer, Bryce, et al. "Arthroscopic Tool Classification using Deep Learning." Proceedings of the 2020 the 4th International Conference on Information System and Data Mining. 2020. (Year: 2020).*

Ångman, Mikael, and Hampus Viken. "Automatic segmentation of articular cartilage in arthroscopic images using deep neural networks and multifractal analysis." (2020). (Year: 2020).*

International Preliminary Report on Patentability dated Jul. 4, 2023, directed to International Application No. PCT/US2021/073160; 12 pages.

International Search Report and Written Opinion mailed Jun. 21, 2022, directed to International Application No. PCT/US2021/073160; 19 pages.

Invitation to Pay Additional Fees, and Where Applicable, Protest Fee mailed Apr. 29, 2022, directed to International Application No. PCT/US2021/073160; 13 pages.

* cited by examiner

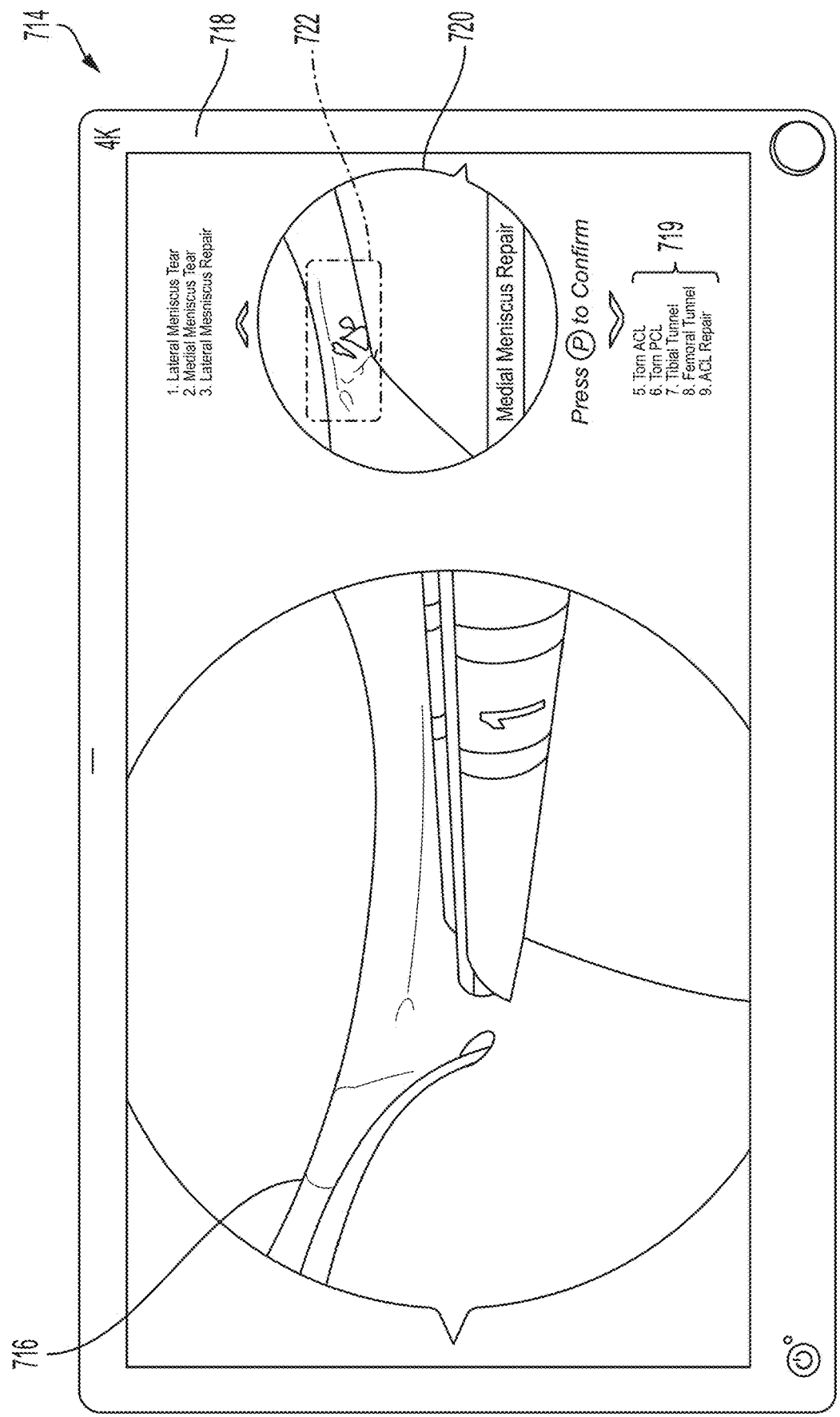

SYSTEMS AND METHODS FOR CLASSIFYING AND ANNOTATING IMAGES TAKEN DURING A MEDICAL PROCEDURE

CROSS-REFERENCE TO RELATED APPLICATIONS

This application claims the benefit of U.S. Provisional Application No. 63/132,445, filed Dec. 30, 2020, the entire contents of which are hereby incorporated by reference herein.

FIELD

This disclosure relates to imaging performed during a surgical procedure, and more specifically, to classifying and annotating images taken during a surgical procedure to provide additional information to a view of the images.

BACKGROUND

Minimally invasive surgery generally involves the use of a high-definition camera coupled to an endoscope inserted into a patient to provide a surgeon with a clear and precise view within the body.

The endoscope emits light from its distal end to illuminate the surgical cavity and receives light reflected or emitted by tissue within the surgical cavity through a lens or window located at the distal end of the endoscope. The endoscope allows the surgeon or practitioner to visualize an internal portion of the patient without requiring the surgeon to expose the portion so that they can view it. During a procedure involving an endoscope, the endoscope provides a video feed that can be recorded and played back at a later time, thus allowing the surgeon or even the patient to view the procedure after the fact. During a surgical procedure involving an endoscope, a patient may not be able to view the video feed in real time as they may be incapacitated during the procedure or otherwise are unable to view the feed while the surgeon is performing the surgical procedure. The surgeon, wanting to inform the patient as to what they found during the procedure and also wanting to inform the patient as to the remedial actions taken during the procedure, may want to use the recorded video feed generated by the endoscope to provide the patient with a visual report. To do so, the surgeon may replay the video feed recorded during the procedure and isolate one or more images (i.e., screen captures) from the video feed and provide them to the patient after the procedure so that the patient can be informed about what took place during the procedure.

Isolating images can be a labor intensive task. The surgeon may have to review hours of footage recorded from the endoscope during the procedure so as to identify images that clearly visualize what the surgeon wants the patient to see. The process of identifying images may be further complicated by visual disturbances experienced by the endoscope during the procedure. For instance, blood, turbidity, smoke, and other phenomenon that inhibit the visualization of the internal portion of the patient, may require the surgeon to sift through video data to find a clear shot that the surgeon can provide to the patient so that they can see what took place during the procedure. Thus, the process of finding the visualizations to provide to the patient may take a significant amount of time, and may be so labor intensive, that the surgeon either provides the patient with a subpar image or doesn't provide any image to the patient at all because they don't have the time to do so.

Simply providing the patient with images taken from the endoscope may not adequately inform the patient as to what took place during the procedure, because it is not evident to a layperson what any particular image is showing. Thus, simply providing images from an endoscopic procedure to a patient is not enough to fully inform the patient about the surgical procedure that took place. Thus, often times, the surgeon in addition to reviewing the video feed and isolating images to show the patient after the procedure is completed, also has to go through the selected images and provide annotations to those images so that the lay patient can understand what the image being provided is showing. Often times, the surgeon may simply annotate images by hand using a marker or other writing implement to identify what a particular image is showing. The process of annotating images by hand can even be more labor intensive than the process of selecting the images to include in a report. In manually annotating images, the surgeon has to review the image, determine what is being shown in the image, and then decide upon the best way to annotate the image so that the patient can understand what the image is showing.

If the writing is not clear, the patient may still not comprehend what they are looking at, despite the time and effort expended by the surgeon to provide the patient with the images. Thus, in order to provide the patient with a report post-surgery using images captured from an endoscopic video feed, the surgeon can be required to spend a significant amount time to annotate the images in a way that the patient can understand what they are looking at. This time-intensive process can be a source of great burden to a surgeon whose schedule and time may already be stretched thin. Thus, the process of providing visualizations to a patient may be not only ineffective in informing the patient about their procedure, but may also take precious time out of a surgeon's already busy schedule.

SUMMARY

In one or more examples, annotations are automatically applied to one or more images captured during a surgical procedure using an imaging tool. In one or more examples, the annotations can be generated by applying one or more machine learning classifiers to the images to determine the presence of various features contained within the images. Optionally, the machine learning classifiers can be configured to determine the anatomy displayed in a particular image as well as the procedure step shown in a given image. Using these two determinations, the systems and methods described herein can generate one or more annotations that are then overlaid on or laid next to an image so as to provide the patient or other person viewing the image with context as to what the image is showing. Using machine learning classifiers to extract features from the images taken during a surgical procedure can significantly reduce the amount of time that a surgeon has to spend reviewing images post-surgery for the purpose of providing them to a patient in a report. Furthermore, the systems and methods described herein can further reduce the time spent generating a post-surgical report by automatically generating the annotations and laying them out vis-à-vis the image in a way that clearly conveys the context of the image so that the patient can understand what is being shown in the image.

In one or more examples, a surgeon or other practitioner can select an annotations template prior to performing a surgery. Based on which template is selected the surgeon can be prompted to capture one or more images in a specified order based on one or more image slots associated with the template. The image slots can be associated with one or more annotations on a surgical report that provide context about the image. Thus, the annotations define what image should be supplied in a given image slot, and the surgeon is directed to capture an image during the surgery that matches what is described by the annotations. In this way, the surgeon saves time post-surgery by not having to go through and select images to provide in a patient report, and saves time by not having to generate the annotations since the systems and methods described herein automatically generate the annotations based on the template selected by the patient before the surgery.

In one or more examples, a method for annotating one or more images generated during a surgical procedure to provide additional information to a viewer of the images includes receiving video data captured from an imaging tool configured to image an internal portion of a patient, converting the received video data into a plurality of image frames, applying one or more machine learning classifiers to the received video data to generate one or more classification metrics based on the received video data, wherein the one or more machine learning classifiers are created using a supervised training process that comprises using one or more annotated images to train the machine learning classifier, identifying one or more characteristics in one or more of the image frames of the plurality of image frames based on the generated one or more classification metrics, and creating one or more annotations that provide additional information to a viewer of the one or more images based on the identified one or more characteristics, and displaying the one or more annotations with the one or more image frames.

Optionally, the supervised training process includes applying one or more identifiers to each image of a plurality of images to indicate one or more characteristics associated with the image, and processing each image of the plurality of images and its corresponding one or more identifiers.

Optionally, the one or more machine learning classifiers comprises a joint type machine learning classifier configured to generate one or more classification metrics associated with identifying a type of joint pictured in the received video data.

Optionally, the joint type machine learning classifier is trained using one or more training images, each training image including an identifier associated with a type of joint pictured in the training image.

Optionally, the joint type machine learning classifier is configured to identify joints selected from the group consisting of a hip, a shoulder, and a knee.

Optionally, the joint type machine learning classifier is configured to generate one or more classification metrics associated with identifying whether the imaging tool is not within a joint.

Optionally, the one or more machine learning classifiers include a procedure stage machine learning classifier configured to generate one or more classification metrics associated with identifying a procedure stage being performed in the received video data.

Optionally, the procedure stage machine learning classifier is trained using one or more training images, each training image including an identifier associated with a surgical procedure pictured in the training image.

Optionally, identifying a procedure stage being performed comprises identifying whether the received video takes place before or after a surgical repair procedure has been completed.

Optionally, converting the received video data into a plurality of image frames comprises, for each image frame of the plurality of image frames, cropping and reducing a size of the image.

Optionally, the method comprises determining whether the user accepts or rejects the annotated one or more image frames.

Optionally, the method comprises using the user's acceptance or rejection of the annotated one or more image frames to further train the one or more machine learning classifiers.

Optionally, the one or more machine learning classifiers include an image clarity machine learning classifier configured to generate one or more classification metrics associated with a clarity of the received video data.

Optionally, the image clarity machine classifier is configured to generate one or more classification metrics associated with an amount of blood visible in the received video data.

Optionally, the image clarity machine classifier is configured to generate one or more classification metrics associated with an amount of bubbles visible in the received video data.

Optionally, the image clarity machine classifier is configured to generate one or more classification metrics associated with an amount of debris visible in the received video data.

Optionally, identifying one or more characteristics in the one or more of the image frames of the plurality of image frames based on the generated one or more classification metrics comprises determining if a clarity of the video is above a pre-determined threshold, and wherein the determination is based on the one more classification metrics generated by the image clarity machine classifier.

Optionally, the one or more machine learning classifiers are implemented using one or more convolutional neural networks (CNNs).

In one or more examples, a method for annotating one or more images generated during a surgical procedure to provide additional information to a viewer of the images includes receiving a selection of one or more annotation templates from a plurality of annotation templates, wherein each annotation template comprises one or more image slots and wherein each image slot has one or more annotations associated with the image slot that provide additional information to a viewer, receiving video data captured from an imaging tool configured to image an internal portion of a patient, receiving an indication to capture an image frame from the received video, capturing the image from a portion of the received video data based on the received indication, associating the image with an image slot of an annotation template and the one or more annotations associated with the image slot, and displaying the one or more annotations with the one or more image frames.

Optionally, the one or more textual annotations comprise text identifying a joint selected from the group consisting of a hip, a shoulder, and a knee.

Optionally, the one or more annotations comprise text identifying a procedure stage being performed in the received video data.

Optionally, the text identifying a procedure stage being performed comprises text identifying whether the received video takes place before or after a surgical repair procedure has been completed.

Optionally, the procedure stage comprises procedures selected from the group consisting of a labrum repair, a cam resection, and a rotator cuff repair.

Optionally, capturing the image from the portion of the received video data comprises cropping and reducing a size of the image.

Optionally, the method comprises determining whether the user accepts or rejects the image.

In one or more examples, a system for annotating one or more images generated during a surgical procedure to provide additional information to a viewer of the images includes a memory, one or more processors, wherein the memory stores one or more programs that when executed by the one or more processors, cause the one or more processors to receive video data captured from an imaging tool configured to image an internal portion of a patient, convert the received video data into a plurality of image frames, apply one or more machine learning classifiers to the received video data to generate one or more classification metrics based on the received video data, wherein the one or more machine learning classifiers are created using a supervised training process that comprises using one or more annotated images to train the machine learning classifier, identify one or more characteristics in one or more of the image frames of the plurality of image frames based on the generated one or more classification metrics, create one or more annotations that provide additional information to a viewer of the one or more images based on the identified one or more characteristics, and display the one or more annotations with the one or more image frames.

Optionally, the supervised training process includes applying one or more identifiers to each image of a plurality of images to indicate one or more characteristics associated with the image, and processing each image of the plurality of images and its corresponding one or more identifiers.

Optionally, the one or more machine learning classifiers comprises a joint type machine learning classifier configured to generate one or more classification metrics associated with identifying a type of joint pictured in the received video data.

Optionally, the joint type machine learning classifier is trained using one or more training images, each training image including an identifier associated with a type of joint pictured in the training image.

Optionally, the joint type machine learning classifier is configured to identify joints selected from the group consisting of a hip, a shoulder, and a knee.

Optionally, the joint type machine learning classifier is configured to generate one or more classification metrics associated with identifying whether the imaging tool is not within a joint.

Optionally, the one or more machine learning classifiers include a procedure stage machine learning classifier configured to generate one or more classification metrics associated with identifying a procedure stage being performed in the received video data.

Optionally, the procedure stage machine learning classifier is trained using one or more training images, each training image including an identifier associated with a surgical procedure pictured in the training image.

Optionally, identifying a procedure stage being performed comprises identifying whether the received video takes place before or after a surgical repair procedure has been completed.

Optionally, converting the received video data into a plurality of image frames comprises, for each image frame of the plurality of image frames, cropping and reducing a size of the image.

Optionally, the method comprises determining whether the user accepts or rejects the annotated one or more image frames.

Optionally, the method comprises using the user's acceptance or rejection of the annotated one or more image frames to further train the one or more machine learning classifiers.

Optionally, the one or more machine learning classifiers include an image clarity machine learning classifier configured to generate one or more classification metrics associated with a clarity of the received video data.

Optionally, the image clarity machine classifier is configured to generate one or more classification metrics associated with an amount of blood visible in the received video data.

Optionally, the image clarity machine learning classifier is configured to generate one or more classification metrics associated with an amount of bubbles visible in the received video data.

Optionally, the image clarity machine learning classifier is configured to generate one or more classification metrics associated with an amount of debris visible in the received video data.

Optionally, identifying one or more characteristics in the one or more of the image frames of the plurality of image frames based on the generated one or more classification metrics comprises determining if a clarity of the video is above a pre-determined threshold, and wherein the determination is based on the one more classification metrics generated by the image clarity machine classifier.

Optionally, the one or more machine learning classifiers are implemented using one or more convolutional neural networks (CNNs).

In one or more examples, a system for annotating one or more images generated during a surgical procedure to provide additional information to a viewer of the images includes a memory, one or more processors, wherein the memory stores one or more programs that when executed by the one or more processors, cause the one or more processors to receive a selection of one or more annotation templates from a plurality of annotation templates, wherein each annotation template comprises one or more image slots and wherein each image slot has one or more annotations associated with the image slot that provide additional information to a viewer, receiving video data captured from an imaging tool configured to image an internal portion of a patient, receive an indication to capture an image frame from the received video, capture the image from a portion of the received video data based on the received indication, associate the image with an image slot of an annotation template and the one or more annotations associated with the image slot, and displaying the one or more annotations with the one or more image frames.

Optionally, the one or more textual annotations comprise text identifying a joint selected from the group consisting of a hip, a shoulder, and a knee.

Optionally, the one or more annotations comprise text identifying a procedure stage being performed in the received video data.

Optionally, the text identifying a procedure stage being performed comprises text identifying whether the received video takes place before or after a surgical repair procedure has been completed.

Optionally, the procedure stage comprises procedures selected from the group consisting of a labrum repair, a cam resection, and a rotator cuff repair. Optionally, capturing the image from the portion of the received video data comprises cropping and reducing a size of the image.

Optionally, the processor is further caused to determine whether the user accepts or rejects the image.

In one or more examples, a non-transitory computer readable storage medium storing one or more programs for execution by one or more processors of an electronic device that when executed by the device, cause the device to receive video data captured from an imaging tool configured to image an internal portion of a patient, convert the received video data into a plurality of image frames, apply one or more machine learning classifiers to the received video data to generate one or more classification metrics based on the received video data, wherein the one or more machine learning classifiers are created using a supervised training process that comprises using one or more annotated images to train the machine learning classifier, identify one or more characteristics in one or more of the image frames of the plurality of image frames based on the generated one or more classification metrics, create one or more annotations that provide additional information to a viewer of the one or more images based on the identified one or more characteristics, and display the one or more annotations with the one or more image frames. According to an aspect, a computer program product is provided comprising instructions which, when executed by one or more processors of an electronic device, cause the device to receive video data captured from an imaging tool configured to image an internal portion of a patient, convert the received video data into a plurality of image frames, apply one or more machine learning classifiers to the received video data to generate one or more classification metrics based on the received video data, wherein the one or more machine learning classifiers are created using a supervised training process that comprises using one or more annotated images to train the machine learning classifier, identify one or more characteristics in one or more of the image frames of the plurality of image frames based on the generated one or more classification metrics, create one or more annotations that provide additional information to a viewer of the one or more images based on the identified one or more characteristics, and display the one or more annotations with the one or more image frames.

It will be appreciated that any of the aspects, features and options described in view of any the systems described above apply equally to the corresponding methods and computer-readable storage mediums, and vice versa. It will also be clear that any one or more of the characteristics of any one or more of the systems, methods, and/or computer-readable storage mediums recited above may be combined, in whole or in part, with one another and/or with any other features or characteristics described elsewhere herein.

Optionally, the supervised training process includes applying one or more identifiers to each image of a plurality of images to indicate one or more characteristics associated with the image, and processing each image of the plurality of images and its corresponding one or more identifiers.

Optionally, the one or more machine learning classifiers comprises a joint type machine learning classifier configured to generate one or more classification metrics associated with identifying a type of joint pictured in the received video data.

Optionally, the joint type machine learning classifier is trained using one or more training images, each training image including an identifier associated with a type of joint pictured in the training image.

Optionally, the joint type machine learning classifier is configured to identify joints selected from the group consisting of a hip, a shoulder, and a knee.

Optionally, the joint type machine learning classifier is configured to generate one or more classification metrics associated with identifying whether the imaging tool is not within a joint.

Optionally, the one or more machine learning classifiers include a procedure stage machine learning classifier configured to generate one or more classification metrics associated with identifying a procedure stage being performed in the received video data.

Optionally, the procedure stage machine learning classifier is trained using one or more training images, each training image including an identifier associated with a surgical procedure pictured in the training image.

Optionally, identifying a procedure stage being performed comprises identifying whether the received video takes place before or after a surgical repair procedure has been completed.

Optionally, converting the received video data into a plurality of image frames comprises, for each image frame of the plurality of image frames, cropping and reducing a size of the image.

Optionally, the method comprises determining whether the user accepts or rejects the annotated one or more image frames.

Optionally, the method comprises using the user's acceptance or rejection of the annotated one or more image frames to further train the one or more machine learning classifiers.

Optionally, the one or more machine learning classifiers include an image clarity machine learning classifier configured to generate one or more classification metrics associated with a clarity of the received video data.

Optionally, the image clarity machine classifier is configured to generate one or more classification metrics associated with an amount of blood visible in the received video data.

Optionally, the image clarity machine classifier is configured to generate one or more classification metrics associated with an amount of bubbles visible in the received video data.

Optionally, the image clarity machine classifier is configured to generate one or more classification metrics associated with an amount of debris visible in the received video data.

Optionally, identifying one or more characteristics in the one or more of the image frames of the plurality of image frames based on the generated one or more classification metrics comprises determining if a clarity of the video is above a pre-determined threshold, and wherein the determination is based on the one more classification metrics generated by the image clarity machine classifier.

Optionally, the one or more machine learning classifiers are implemented using one or more convolutional neural networks (CNNs).

In one or more examples. A non-transitory computer readable storage medium storing one or more programs for execution by one or more processors of an electronic device that when executed by the device, causes the device to receive a selection of one or more annotation templates from a plurality of annotation templates, wherein each annotation template comprises one or more image slots and wherein each image slot has one or more annotations associated with the image slot that provide additional information to a viewer, receive video data captured from an imaging tool configured to image an internal portion of a patient, receive an indication to capture an image frame from the received video, capture the image from a portion of the received video data based on the received indication, associate the image with an image slot of an annotation template and the one or more annotations associated with the image slot, and display the one or more annotations with the one or more image frames.

Optionally, the one or more textual annotations comprise text identifying a joint selected from the group consisting of a hip, a shoulder, and a knee.

Optionally, the one or more annotations comprise text identifying a procedure stage being performed in the received video data.

Optionally, the text identifying a procedure stage being performed comprises text identifying whether the received video takes place before or after a surgical repair procedure has been completed.

Optionally, the procedure stage comprises procedures selected from the group consisting of a labrum repair, a cam resection, and a rotator cuff repair.

Optionally, capturing the image from the portion of the received video data comprises cropping and reducing a size of the image.

Optionally, the device is further caused to determine whether the user accepts or rejects the image.

It will be appreciated that any of the variations, aspects, features and options described in view of the systems apply equally to the methods and vice versa. It will also be clear that any one or more of the above variations, aspects, features and options can be combined.

BRIEF DESCRIPTION OF THE FIGURES

The invention will now be described, by way of example only, with reference to the accompanying drawings, in which:

FIG. 7B illustrates another exemplary annotation template according to examples of the disclosure.

DETAILED DESCRIPTION

Figure 1:
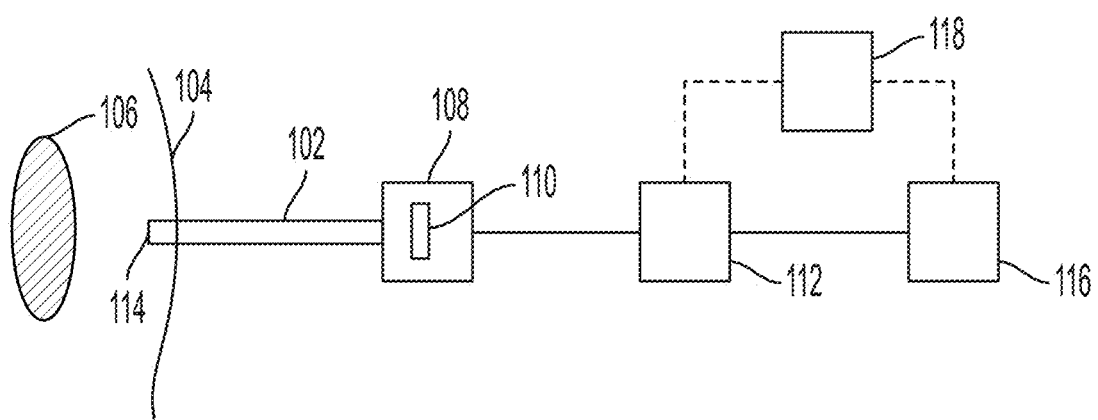
FIG. 1 illustrates an exemplary endoscopy system according to examples of the disclosure.

Reference will now be made in detail to implementations and examples of the disclosure of various aspects and variations of systems and methods described herein. Although several exemplary variations of the systems and methods are described herein, other variations of the systems and methods described herein may include aspects of the systems and methods described herein combined in any suitable manner having combinations of all or some of the aspects described.

Described herein are systems and methods for automatically annotating one or more images generated during a medical procedure to provide additional information to a viewer of the images. According to various examples of the disclosure, one or more images are captured from a video feed recorded from an endoscope during a surgical procedure. The captured images are then processed by one or more machine learning classifiers that are configured to generate classification metrics that are used to determine characteristics about the images such as the anatomy visualized in the images as well as the specific procedure step in the surgery being performed in the captured images. The processing of the images can be performed after the surgical procedure. Based on the generated classification metrics, a determination is made regarding what the captured images illustrate. Based on this determination, the images are annotated so that they can be included with the image, when the image is presented to a patient or other stakeholder, so that the patient can be informed as to what the image is showing. In one or more examples, annotating an image can include appending metadata to the image that identifies the anatomy of the image as well as the procedural step that is illustrated in the image. Additionally or alternatively, annotating an image can also include applying a text annotation that is overlaid or placed to the side of the image in a report that identifies the pertinent characteristics of the image.

According to various examples of the disclosure, the machine learning classifiers can be generated using a supervised training process. According to various examples of the disclosure, the supervised training process can include the use of training images that are annotated with the known characteristics of the image. These training images (i.e., images that contain known characteristics and are identified as such through the annotations) can be then processed by the machine classifiers so as to configure each of the machine classifiers. According to various examples of the disclosure, the machine learning classifiers can include a joint type machine learning classifier that is generated using training images of endoscopic images that are annotated (i.e., identified) with the type of joint illustrated in the training image. According to various examples of the disclosure, the machine learning classifiers can include a procedure stage machine learning classifier that is generated using training images that are annotated with the procedure step illustrated in the training image. In addition to identifying the joint type and the procedure step, one or more of the machine learning classifiers can be configured to determine the clarity of a given image. For example, the machine learning classifiers can be used to determine the amount of blood, bubbles, debris, or other visual impediments that can affect the clarity of a given image. According to various examples of the disclosure, the machine learning classifiers are implemented using one or more convolutional neural networks (CNN).

According to various examples of the disclosure, a surgeon or other practitioner can pre-select an annotation template that includes one or more pre-defined image slots prior to performing a surgical procedure using the endoscope. Each pre-defined image slot can be associated with a particular joint type and procedure step of a surgical procedure. During the endoscopic procedure, the surgeon can capture an image that they determine to correspond to a pre-defined image slot. The captured image can then be annotated with the information corresponding to the pre-defined image slot for which the image was captured.

According to various examples of the disclosure, annotating a captured image can include overlaying the annotations at pre-defined locations on the image and placing a pre-defined graphic corresponding to the identified characteristics of the image to better illustrate the anatomy and procedural step contained within the image.

By automatically detecting characteristics of a captured image and applying annotations to the image to identify those characteristics, the surgeon can provide a comprehensive report to the patient or stakeholder that not only shows the patient what took place during a given surgical procedure, but provides the patient with additional information to help them understand the image they are seeing. Because the images are automatically annotated, the surgeon does not have to expend time and effort to annotate the images by hand after the surgery and can provide the patient with a clear and accurate visual summary of what took place during the surgery.

In the following description of the various examples of the disclosure, it is to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Certain aspects of the present disclosure include process steps and instructions described herein in the form of an algorithm. It should be noted that the process steps and instructions of the present disclosure could be embodied in software, firmware, or hardware and, when embodied in software, could be downloaded to reside on and be operated from different platforms used by a variety of operating systems. Unless specifically stated otherwise as apparent from the following discussion, it is appreciated that, throughout the description, discussions utilizing terms such as "processing," "computing," "calculating," "determining," "displaying," "generating" or the like, refer to the action and processes of a computer system, or similar electronic computing device, that manipulates and transforms data represented as physical (electronic) quantities within the computer system memories or registers or other such information storage, transmission, or display devices.

The present disclosure in some examples of the disclosure also relates to a device for performing the operations herein. This device may be specially constructed for the required purposes, or it may comprise a general purpose computer selectively activated or reconfigured by a computer program stored in the computer. Such a computer program may be stored in a non-transitory, computer readable storage medium, such as, but not limited to, any type of disk, including floppy disks, USB flash drives, external hard drives, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each connected to a computer system bus. Furthermore, the computing systems referred to in the specification may include a single processor or may be architectures employing multiple processor designs, such as for performing different functions or for increased computing capability.

Suitable processors include central processing units (CPUs), graphical processing units (GPUs), field programmable gate arrays (FPGAs), and ASICs.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the present disclosure as described herein.

FIG. 1 illustrates a system 100 for automatically annotating images captured during an endoscopic surgical procedure, according to examples of the disclosure. System 100 includes an endoscope 102 for insertion into a surgical cavity 104 for imaging tissue 106 within the surgical cavity 104 during a medical procedure. The endoscope 102 may extend from an endoscopic camera head 108 that includes one or more imaging sensors 110 bight reflected and/or emitted (such as fluorescence light emitted by fluorescing targets that are excited by fluorescence excitation illumination light) from the tissue 106 is received by the distal end 114 of the endoscope 102. The light is propagated by the endoscope 102, such as via one or more optical components (for example, one or more lenses, prisms, light pipes, or other optical components), to the camera head 108, where it is directed onto the one or more imaging sensors 110. In one or more examples, one or more filters (not shown) may be included in the endoscope 102 and/or camera head 108 for filtering a portion of the light received from the tissue 106 (such as fluorescence excitation light).

The one or more imaging sensors 110 generate pixel data that can be transmitted to a camera control unit 112 that is communicatively connected to the camera head 108. The camera control unit 112 generates a video feed from the pixel data that shows the tissue being viewed by the camera at any given moment in time. In one or more examples, the video feed can be transmitted to an image processing unit 116 for further image processing, storage, display, and/or routing to an external device (not shown). The images can be transmitted to one or more displays 118, from the camera control unit 112 and/or the image processing unit 116, for visualization by medical personnel, such as by a surgeon for visualizing the surgical field 104 during a surgical procedure on a patient.

As will be described in further detail below, the imaging processing unit 116 can be configured to perform the methods described below for annotating images captured during a surgical procedure captured by the one or more image sensors 110. In one or more examples, and as discussed in further detail below, the imaging processing unit 116 can be configured to make classifications of and annotate image data or alternatively can be configured to transmit images to an external processor (such as one hosted on a cloud computing service) for processing to generate the annotations.

It may not be readily apparent to a layperson, such as a patient, what the video and images produced by an endoscope during a surgical procedure are showing. Often times, understanding what an endoscopic image is portraying requires deeper knowledge of anatomy and medicine than what a layperson may have. Without guidance from a medical professional, a picture taken from an endoscope during a surgical procedure can be meaningless and provides the patient without the intended information that the image was meant to provide.

Figure 2:
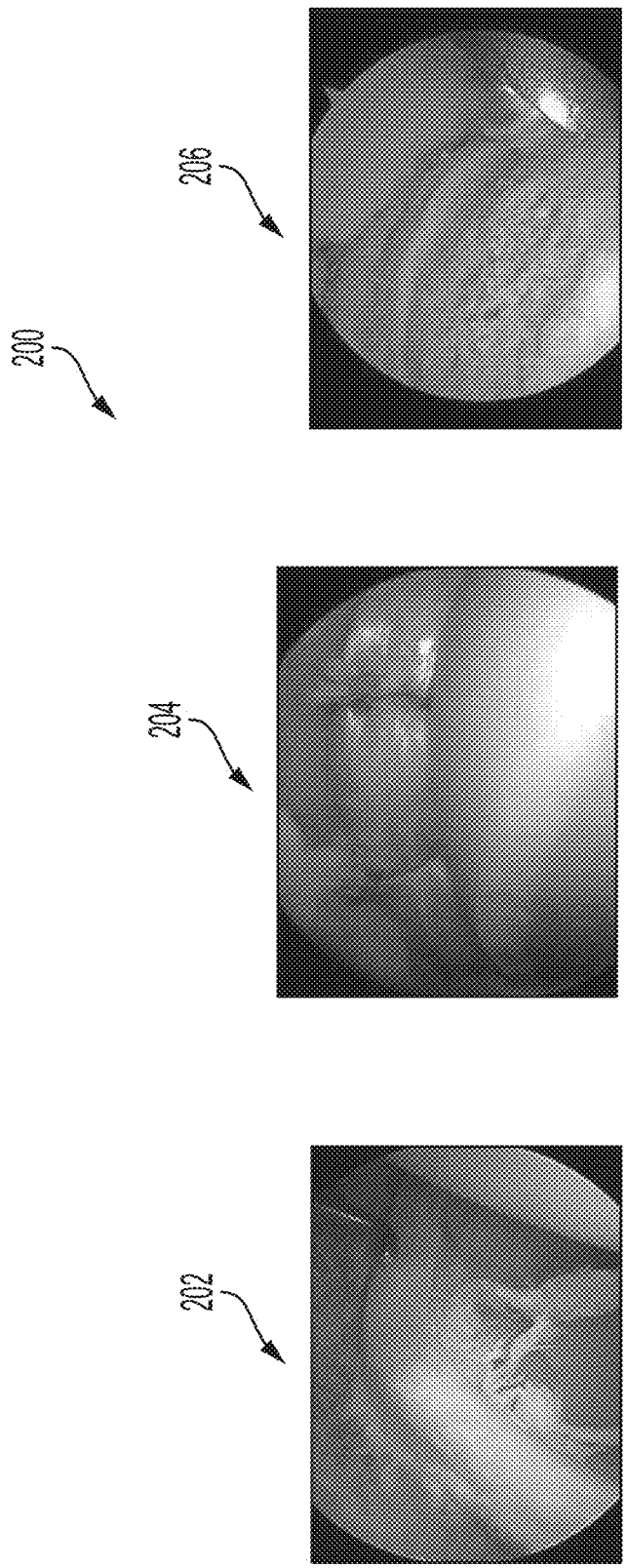
FIG. 2 illustrates exemplary images taken from an endoscope according to examples of the disclosure.

FIG. 2 illustrates exemplary images taken from an endoscope according to examples of the disclosure. In one or more examples, the images 200 illustrated in FIG. 2 represent endoscopic images taken during one or more surgical procedures. For instance, image 202 represents an image taken with an endoscope of a human labrum. A layperson viewing image 202 may not be able to readily ascertain that image 202 shows a labrum. Being able to identify image 202 as showing a labrum, as described above, can require advanced knowledge of anatomy and medicine. Furthermore, even if a patient has knowledge of what a labrum is and knows what a labrum looks like, they may not be able to recognize a labrum as viewed through an endoscope, without having experience viewing endoscopic images.

Even if the patient is able to recognize what anatomy is being shown in a given endoscopic image, they may still not be able to readily ascertain what procedure step in a surgical procedure a given image is portraying. For instance, image 202 of FIG. 2 shows a view of a torn labrum, viewed through an endoscope during a surgical procedure. Even if the patient viewing the image is able to recognize the image as that of a labrum, they may not be able to recognize what state the labrum is in (i.e., what stage of the repair is the labrum in). For instance, while image 202 shows a torn labrum before it has been surgically repaired, image 204 shows the same labrum after it has been repaired. Having a patient understand when they are viewing a torn labrum such as depicted in image 202 versus when they are viewing a repaired labrum such as the one shown in image 204 can be critical information to ensuring that the patient understands how the surgical procedure went.

The above issues with simply providing endoscopic images without annotations can apply to all types of anatomy viewed through an endoscope. For instance, image 206 illustrates a cam resection of a hip joint. A patient viewing image 206 without any provided context may not be able to even identify the image as a hip joint let alone that the image shows a cam resection of the hip joint.

To remedy the above problem, traditionally surgeons or other medical practitioners seeking to provide patients with information about their procedure post-surgery have put together reports about the procedure that includes endoscopic images such as the images 200 of FIG. 2. As a preliminary matter, the surgeon has to first choose which images to provide to the patient. During a surgical procedure, the endoscope is often moving around the internal anatomy of the patient and not all images produced during an endoscopic procedure may adequately illustrate what the practitioner wants the patient to see. Thus, the practitioner is forced to go through the video or image data acquired during the procedure to select images that clearly illustrate what the practitioner wants the patient to see. The process of selecting the images to provide to the patient can thus be a time-consuming effort.

As demonstrated above with respect to the discussion of FIG. 2, simply providing the images to the patient may not be sufficient. Without context, a patient may not be able to understand what the images show. Thus, in order to provide that context, the practitioner after selecting the images for a post-surgery report may also be required to annotate the images to indicate what the selected images show. Often times the surgeon annotates the images by hand, writing a description of the image next to the image itself thereby annotating the image to provide context to the patient. The process of selecting the images for a report and then further having to hand annotate those images can in combination be a time-consuming effort.

Automating the process of selecting and annotating the images provided to a patient post-surgery can relieve the time burden described above. Reducing or eliminating the amount of time that a surgeon has to spend post-surgery to prepare a report can provide a measure of convenience to the surgeon and in some examples can provide information to the patient in a manner that is clearer than if the surgeon hand prepared the report using a process described above. However, automating the process requires two specific steps to be automated. First, the automated process should be able to review and select specific images that will give the patient the information they need to understand how their surgery went. Second, the automated process should be able to automatically annotate the selected images to provide the patient with the information about each image so that the patient can understand what it is they are viewing. By automating these two steps in the process of generating a surgical report, the surgeon can save valuable time compared to the process of having to generate the reports by hand in the method described above.

Figure 3:
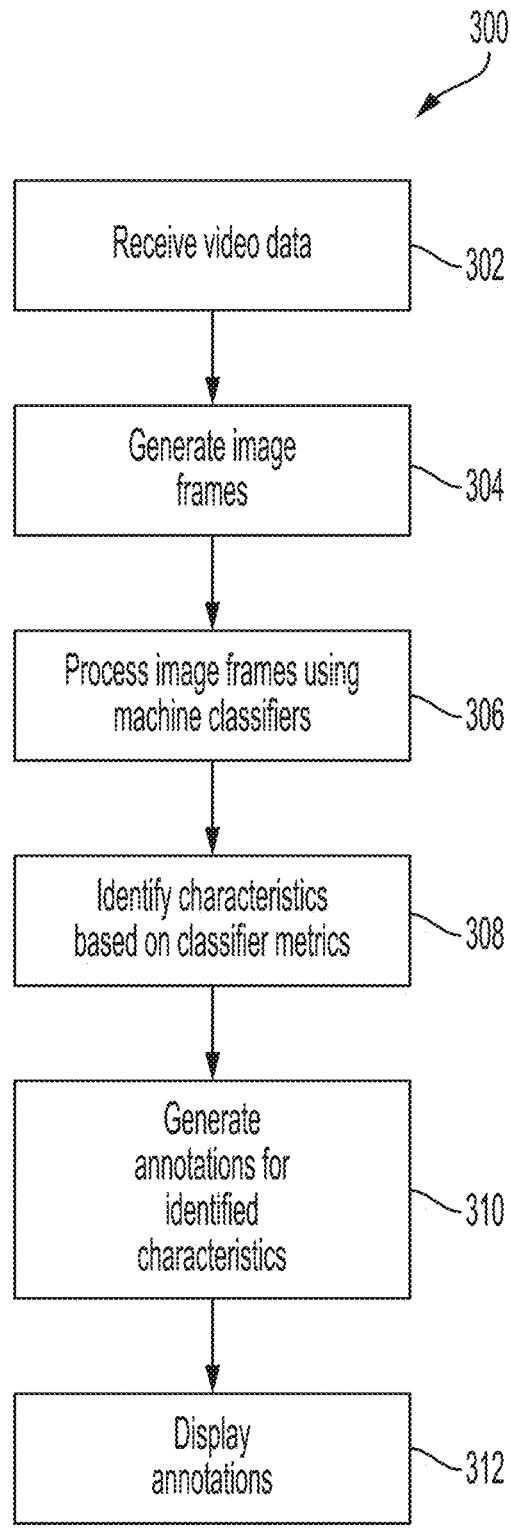
FIG. 3 illustrates an exemplary method for annotating images according to examples of the disclosure.

FIG. 3 illustrates an exemplary method for annotating images according to examples of the disclosure. In one or more examples of the disclosure, the process 300 illustrated in FIG. 3 can begin at step 302 wherein video data from an endoscopic device or other type of imaging device is received. In one or more examples, the video data can be transmitted to one or more processors configured to implement process 300 using a High-Definition Multimedia Interface (HDMI), Digital Visual Interface (DVI) or other interface capable of connecting a video source (such as an endoscopic camera) to a display device or graphics processor.

Once the video data has been received at step 302, the process 300 can move to step 304 wherein one or more image frames can be extracted from the video data. In one or more examples, the image frames can be extracted from the video data in a periodic interval at a pre-determined period automatically. Alternatively or additionally, one or more image frames can be extracted from the video data in response to user input such as for instance the surgeon pushing a button or other user input device to indicate that they want to capture an image from the video data at or around any particular moment in time. In one or more examples, the images can be extracted and stored in a memory according to known image storage standards for memory such as JPEG, GIF, and TIFF image file formats. In one or more examples, the pre-determined time between capturing image frames from the video data can be configured to ensure that an image is captured during each stage in a surgical procedure, thereby ensuring that the captured images will adequately represent all of the steps in a surgical process. In one or more examples, the image frames can be captured from the video data in real-time, i.e., as the surgical process is being performed. Additionally or alternatively, in one or more examples, the images can be captured from the video data post-surgery. In one or more examples, and as part of step 304, the captured images can be reduced in size and cropped so as to reduce the amount of memory required to store a captured image Once the image frames have been captured in step 304, the process 300 can move to step 306 wherein the image frames are processed using one or more machine learning classifiers that are configured to determine whether the captured image includes one or more characteristics. In one or more examples, the one or more machine learning classifiers can be configured to automate the process of identifying which images of the one or more images include features or characteristics that the surgeon would want to the patient to see in a post-surgery report.

In one or more examples, the one or more machine classifiers can be configured to identify the anatomy that is being shown in a given image. For instance, and as discussed in further detail below, the one or more machine classifiers can be configured to identify a particular joint type shown in an image such as whether a given image is of a hip, a shoulder, a knee, or any other anatomical feature that can be viewed using an imaging tool such as an endoscope. In one or more examples, and as further discussed in detail below, the one or more machine classifiers can be created using a supervised training process in which one or more training images (i.e., images that are known to contain specific anatomical features) can be used to create a classifier that can determine if an image inputted into the machine classifier contains a particular feature. Alternatively or additionally, the one or more machine learning classifiers can be configured to determine a particular surgical step being performed in the image. For instance, and as an example, the one or more machine classifiers can be configured to determine if a particular image shows a torn labrum or instead if the image shows the labrum post-repair.

In one or more examples, multiple machine classifiers can be configured to work collectively with one another to determine what features are present in a given image. As an example, a first machine learning classifier can be used to determine if a particular anatomical feature is present in a given image. If the machine classifier finds that it is more likely than not that the image contains a particular anatomical feature, then the image can be sent to a corresponding machine learning classifier to determine what procedure step is shown in the image. For instance if it is determined that a particular image shows a hip joint, then that same image can also be sent to a machine learning classifier configured to determine if the image shows a torn labrum as well as a separate machine learning classifier configured to determine if the image shows a labrum post-repair. However, if the machine learning classifier configured to determine if a given image shows a hip joint determines that it is unlikely that the image shows a hip joint, then the process 300 at step 306 may not send that image to a machine classifier corresponding to a procedure step for a surgery involving a hip (i.e., a torn labrum or a repaired labrum).

In one or more examples, the one or more machine classifiers can include one or more image clarity classifiers that are configured to determine how clear or obscured a particular image is. During a surgical procedure certain conditions can obfuscate or make an image unclear. For instance blood, turbidity, bubbles, smoke, or other debris can make the quality of an image poor such that a surgeon may not want to use that image as part of a post-surgical report to be provided to a patient. Thus, in one or more examples, the one or more machine classifiers can be configured to determine if an image is clear enough to be included in a report to a patient.

In one or more examples, the one or more machine classifiers are configured to generate a classification metric that is indicative of whether or not a particular feature (that the machine classifier is configured to determine) exists within a particular image. Thus, rather than making a binary determination (yes or no) as to whether a particular image includes a particular feature, the classification metric can inform the process as to how likely it is that a particular image includes a particular feature. As an example, a machine classifier that is configured to classify whether an image contains a hip joint can output a classification metric in the range of 0 to 1 with 0 indicating that it is extremely unlikely that a particular image shows a hip joint and 1 indicating that it is extremely likely that a particular image shows a hip joint. Intermediate values between 0 and 1 can indicate the likelihood that an image contains a particular feature. For instance if a machine learning classifier outputs a 0.8, it can mean that it is more likely than not that the image shows a hip joint, while a classification metric of 0.1 means that it is not likely that the image contains a hip joint.

In one or more examples, the one or more machine classifiers can be implemented using one or more convolutional neural networks (CNNs). CNNs are a class of deep neural networks that can be especially useful for analyzing visual imagery to determine whether certain features exist in an image. Each CNN used to generate a machine classifier used at step 306 can include one or more layers, with each layer of the CNN configured to aide in the process of determining whether a particular image includes a feature that the overall CNN is configured to determine. Alternatively or additionally, the CNNs can be configured as Region-based Convolutional Networks (R-CNNs) that can not only determine if a particular image contains a feature, but can identify the specific location in the image where the feature is shown. Additionally or alternatively, a manual intervention process may be provided to allow the surgeon to pick the location within the particular image that is appropriate to place an annotation or associate with an annotation. For example, in cases where the one or more machine classifiers are not able to automatically identify a precise location within an image to identify with an annotation (e.g. a precise location of a joint clinical condition on the joint), then a manual intervention process may be provided in a user interface to allow the surgeon to identify on the image the precise location, and to either position the annotation at that location or to otherwise associate the annotation with that location such as by connecting it with an arrow pointing to the location. In one or more examples, based on the specific location in the image where a feature is shown, the system can automatically crop the image to only show the relevant portions of the image associated with a given feature.

Returning to the example of FIG. 3, once the one or more images have been processed by the one or more machine learning classifiers at step 306, the process 300 can move to step 308 wherein a determination is made as to what features are present within a particular image. The determination made at step 308 can be based on the classification metrics output from each of the machine learning classifiers. As an example, each of the classification metrics generated by each of the machine learning classifiers can be compared to one or more pre-determined thresholds, and if the classification metric exceeds the pre-determined threshold than a determination is made that the image contains the feature corresponding to that machine learning classifier. As an example, if a machine learning classifier processing an image outputs a classification metric of 0.7, and the pre-determined threshold is set at 0.5, then at step 308 a determination is made that the image shows a shoulder joint. In one or more examples, a determination can be made for each and every machine learning classifier that the image is processed through.

Once the determinations are made as to what features a particular image contains at step 308, those determinations can be used to generate one or more annotations to be applied to the image at step 310. As discussed above, and as will be described in further detail below, annotating an image in this context can refer to applying text next to or overlaid on an image captured at step 304. Alternatively or additionally, annotating an image can also refer to appending metadata to an image that indicates what features the image was found to contain. In one or more examples, applying annotations to an image can include formatting the report so that the images and their annotations are provided in a specific layout that is configured to make it easy for the patient to understand. In one or more examples, and as further discussed below, annotating an image is not confined to simply applying textual additions to images but can also include placing one or more graphics that are configured to give the patient more information or to make it clear to the patient what the particular endoscopic image is showing.

Once the annotations have been generated at step 310, the process 300 can move to step 312 wherein the annotations are displayed. In one or more examples, displaying the annotations can refer to displaying an image and its corresponding annotations on a display of a computing device such as a computer or a tablet. In one or more examples, displaying the annotations can also refer to generating a print out of the images with their corresponding annotations that is provided to a patient as part of their post-surgery report.

Figure 4:
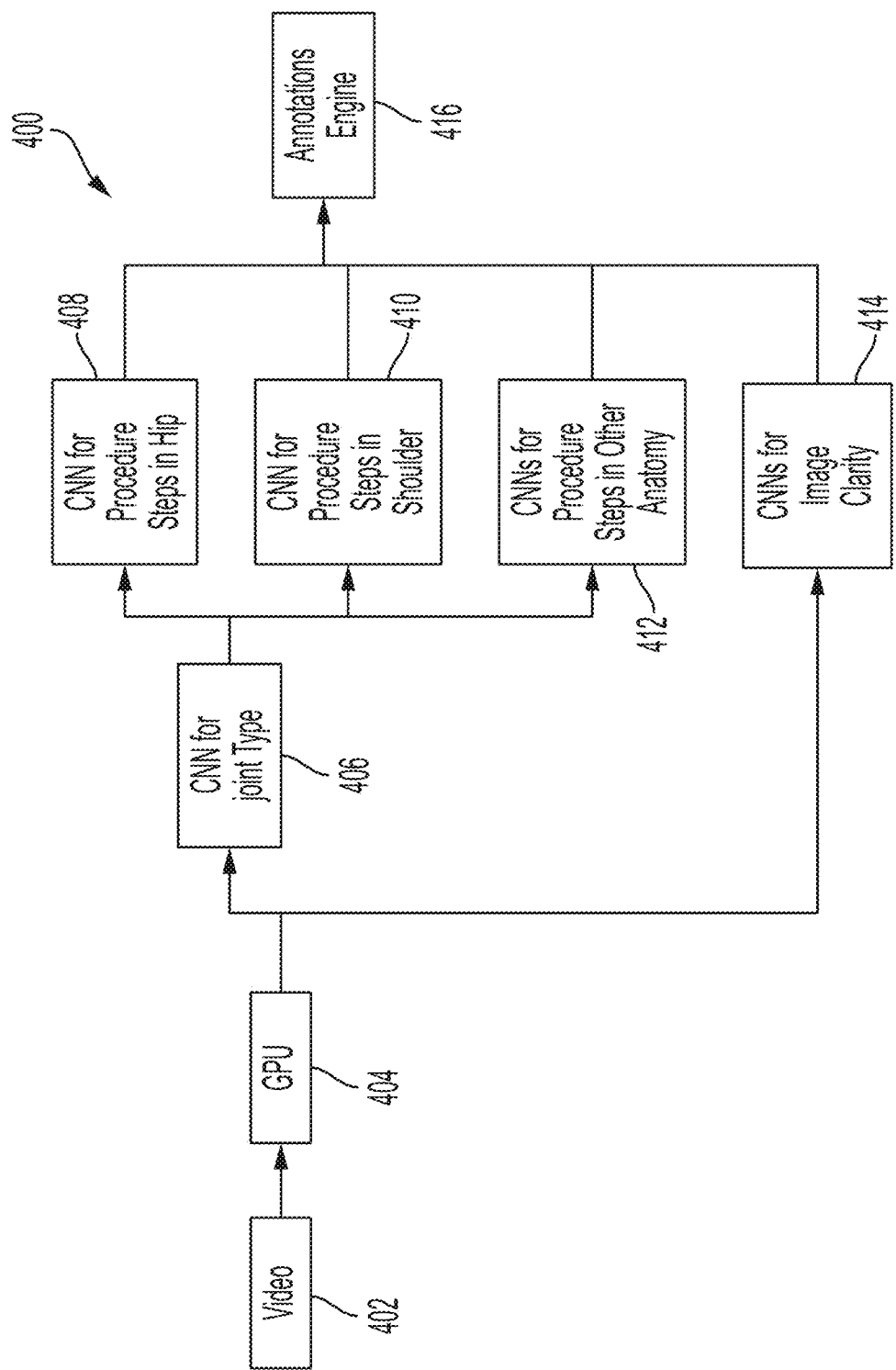
FIG. 4 illustrates an exemplary machine classifier process flow according to examples of the disclosure.

FIG. 4 illustrates an exemplary machine classifier process flow according to examples of the disclosure. In one or more examples, the process flow 400 illustrates an example implementation of the process described above with respect to FIG. 3. In one or more examples, the process can begin with the video data being received as described above at step 302 with respect to FIG. 3. In one or more examples, the video data can be transmitted to a graphics processing unit (GPU) 404, wherein the one or more image frames are generated from the video data as described above with respect to step 304 of FIG. 3.

Once the image frames have been generated at the GPU at 404, the one or more machine classifiers can be applied to the images so as to ultimately determine what annotations (if any) to a apply to a given image. As shown in FIG. 4, in one or more examples, a given image can first be sent to one or more machine learning classifiers (shown in the figure being implemented as a CNN) that are configured to determine the joint type shown in the image. As described above, 406 can be implemented as one or more separate machine learning classifiers configured to determine a joint type shown in the image. In one or more examples, once the image is processed using the one or more machine learning classifiers for joint type at 406, the image can be processed by one or more machine learning classifiers configured to determine the procedure step shown in the image. For instance, if it is determined that the image shows a hip joint (or is likely to show a hip joint) then the image can be sent to a machine learning classifier that is specifically configured to determine a procedure step for procedures that occur in a hip joint as depicted at 408. If however, the image is determined to be of a shoulder joint, then the image can be sent to one or more machine classifiers configured to determine a procedure step for the shoulder as depicted at 410.

Similarly, and as depicted at 412, the image can be sent to one or more machine classifiers configured to determine procedure steps in other anatomical features of the body as depicted at 412. Similarly, the images generated at the GPU 404 can also be sent to a parallel set of machine learning classifiers that are collectively configured to determine the clarity of the image as depicted at 414 and as described above. In one or more examples, the outputs of each of the machine learning classifiers can be sent to an annotations engine 416 wherein a determination is made as to which annotations to apply to the image, and the annotations are ultimately generated.

As described above, the one or more machine learning classifiers can be created using a supervised training process. In a supervised training process, the classifier can be generated by using one or more training images. Each training image can be annotated (i.e., by appending metadata to the image) that identifies one or more characteristics of the image. For instance, using a hip joint machine learning classifier configured to identify the presence of a hip joint in an image as an example, the machine learning classifier can be generated using a plurality of training images known (a priori) to visualize hip joints.

Figure 5:
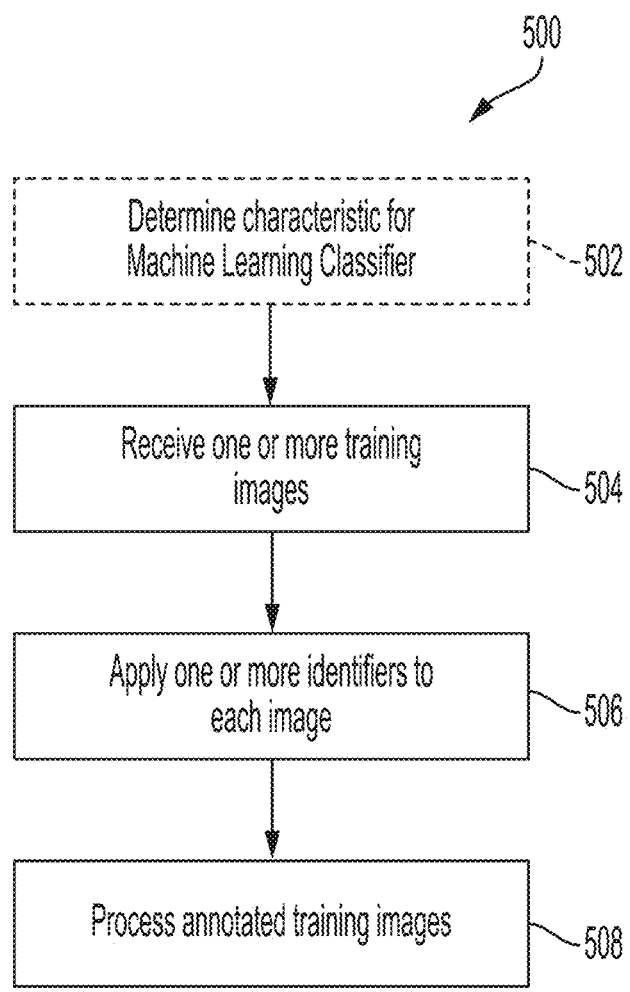
FIG. 5 illustrates an exemplary machine classifier training method according to examples of the disclosure.

FIG. 5 illustrates an exemplary machine classifier training method according to examples of the disclosure. In the example of FIG. 5, the process 500 can begin at step 502 wherein a particular characteristic for a given machine learning classifier is selected or determined. In one or more examples, the characteristics can be selected based on the needs of the surgeons or medical team who plan to use the systems and methods to automatically annotate images taken during a surgery. Thus, for instance, if a particular medical practice only performs procedures involving hip joints, then the characteristics determined or selected at step 502 will include only characteristics germane to hip surgery contexts. In one or more examples, step 502 can be optional, as the selection of characteristics needed for the machine learning classifiers can be selected beforehand in a separate process.

Once the one or more characteristics to be classified have been determined at step 502, the process 500 can move to step 504 wherein one or more training images corresponding to the selected characteristics are received. In one or more examples, each training image can include one or more identifiers that identify the characteristics contained within an image. The identifiers can take the form of annotations that are appended to the metadata data of the image, identifying what characteristics are contained within the image. A particular image of the training image set can include multiple identifiers. For instance a picture of a repaired labrum tear can include a first identifier that indicates the picture contains a hip joint and a separate identifier that indicates the procedure step which in the example is a repaired labrum.

In one or more examples, if the training images received at step 504 do not include identifiers, then the process can move to step 506 wherein one or more identifiers are applied to each image of the one or more training images. In one or more examples, the training images can be annotated with identifiers using a variety of methods. For instance, in one or more examples, the identifiers can be manually applied by a human or humans who view each training image, determine what characteristics are contained within the image, and then annotate the image with the identifiers pertaining to those characteristics. Alternatively or additionally, the training images can be harvested from images that have been previously classified by a machine classifier. For instance, and returning to the examples of FIG. 3, once a machine learning classifier makes a determination as to the characteristics contained within an image at step 308, the image can be annotated with the identified characteristics (i.e., annotated with one or more identifiers) and the image can then be transmitted to and stored in a memory for later use as a training image. In this way, each of the machine learning classifiers can be constantly improved with new training data (i.e., by taking information from previously classified images) so as to improve the overall accuracy of the machine learning classifier.

In one or more examples, and in the case of segmentation or region based classifiers such R-CNNS, the training images can be annotated on a pixel-by-pixel or regional basis to identify the specific pixels or regions of an image that contain specific characteristics. For instance in the case of R-CNN, the annotations can take the form of bounding boxes or segmentations of the training images. Once each training image has one or more identifiers annotated to the image at step 506, the process 500 can move to step 508 wherein the one or more training images are processed by each of the machine learning classifiers in order to train the classifier. In one or more examples, and in the case of CNNs, processing the training images can include building the individual layers of the CNN.

The process described above with respect to FIGS. 3-5 can allow for the process of selecting and annotating images to be fully automatic in the sense that the images can be selected and annotated automatically with minimal intervention and involvement from the surgeon or practitioner. While eliminating or minimizing the amount of human intervention can conserve their time to be spent in other endeavors, partially automating the process may suffice as well. For instance, instead of having the images automatically selected by a machine learning classifier, in one or more examples, the surgeon can select the images to capture for the post-surgery report according to a pre-defined template as described in further detail below.

Figure 6:
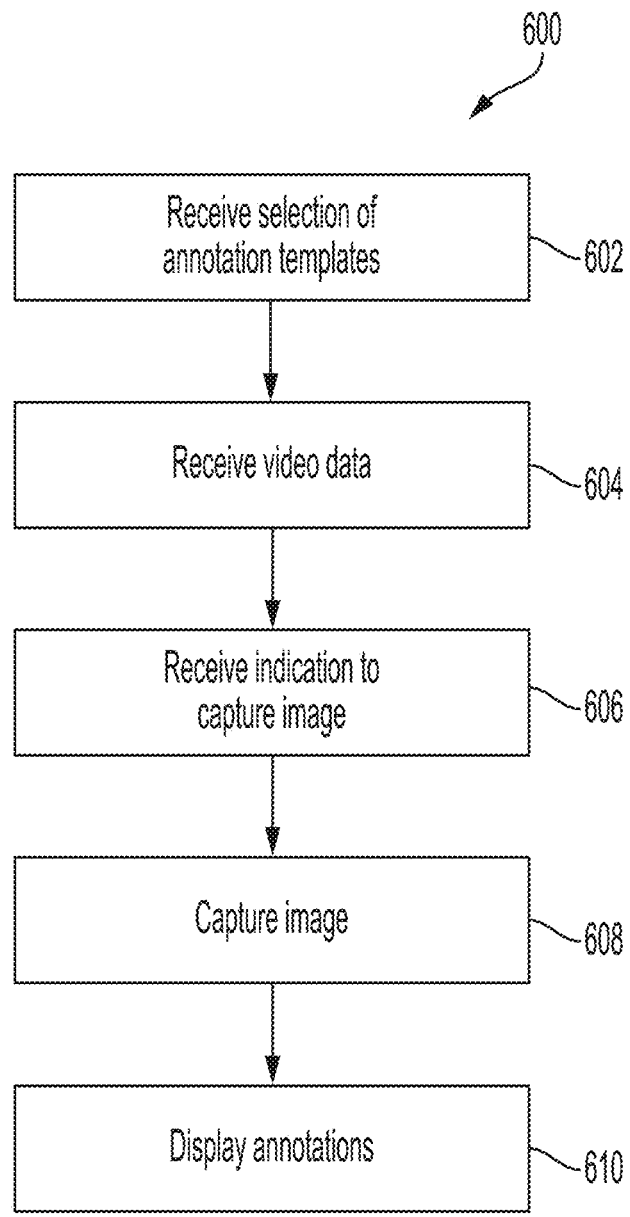
FIG. 6 illustrates another exemplary method for annotating images according to examples of the disclosure.

FIG. 6 illustrates another exemplary method for annotating images according to examples of the disclosure. In one or more examples of the disclosure, the process 600 can begin at step 602 wherein a selection of an annotation template is received. In one or more examples, and as further illustrated below, an annotation template can include a pre-defined surgical report in which the only information not included is the one or more images to be taken during surgery.

Figure 7A:
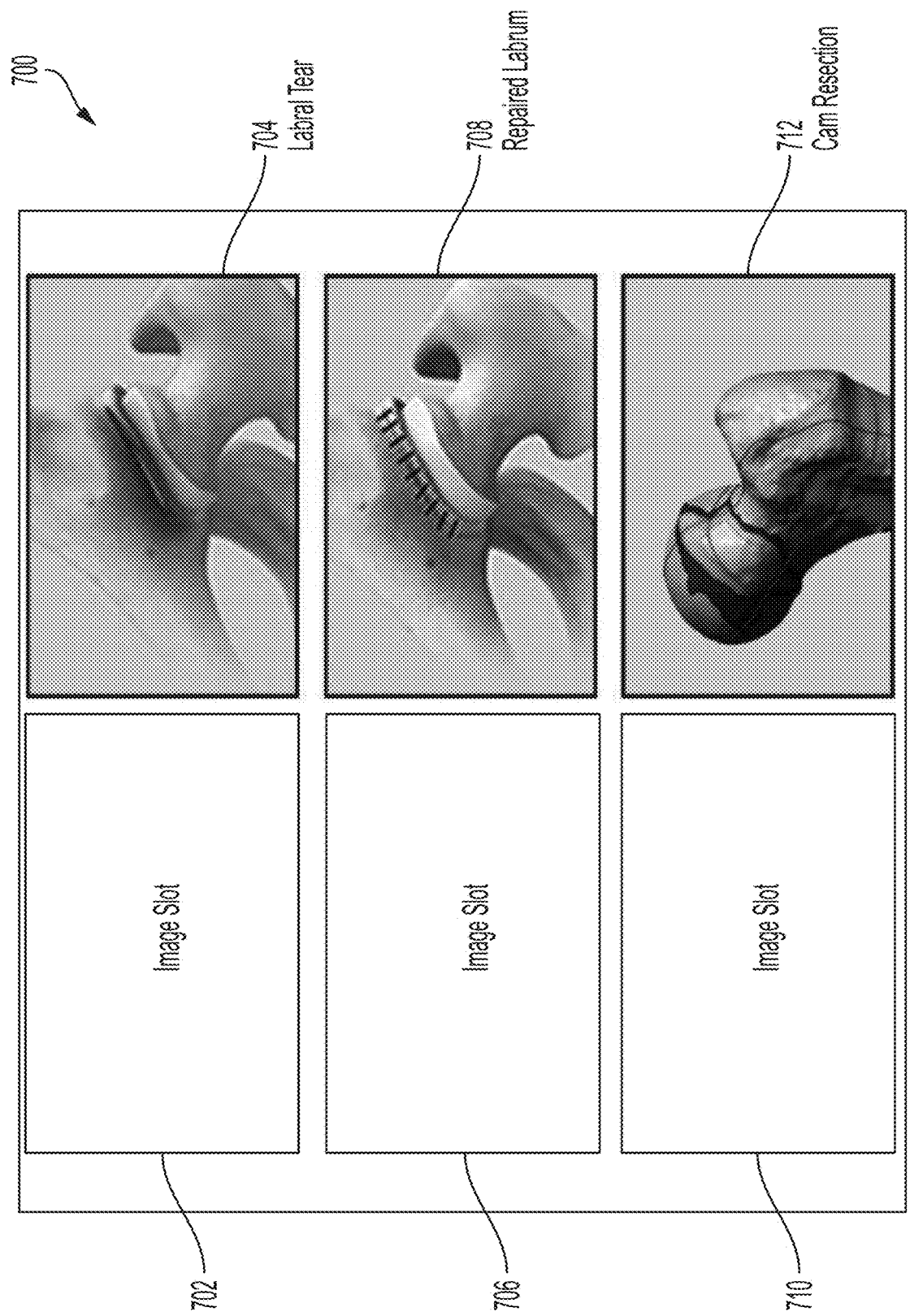
FIG. 7A illustrates an exemplary annotation template according to examples of the disclosure.

FIG. 7A illustrates an exemplary annotation template according to examples of the disclosure. In the example of FIG. 7A, the annotation template 700, can represent two surgical processes: a repair of a torn labrum, and a cam resection. In one or more examples, the template can include all of the annotations already laid out in the format that will ultimately go into the report, with the only missing elements being the pictures that are to be taken during the surgery. For instance, as shown in FIG. 7A, a surgeon can select the template 700 that includes three separate image slots 702, 706, and 710. The image slots 702, 706, and 710 can correspond annotations 704, 708, and 712 respectively.

For instance, the template 700 can include an annotation 704 that will correspond to an image of a labral tear. As will be further described below, during the surgical procedure the surgeon can select and capture an image that will be placed into slot 702 to accompany the annotation of a labral tear 704. Similarly, the template 700 can include an annotation 708 that will correspond to an image of a repaired labrum. During the surgical procedure, the surgeon can select and capture an image to go into the image slot 706 that corresponds to the annotation 708. Finally, the template 700 can include an annotation 712 that will correspond to an image of a cam resection. During the surgical procedure, the surgeon can select and capture an image to go into the image slot 710 that corresponds to the annotation 712.

Returning to the example of FIG. 6, once a template (such as the one described above) is selected by a surgeon, the process 600 can move to step 604 wherein video data is received from an imaging device such as an endoscope. In one or more examples of the disclosure, the received video data can be stored in a memory and/or displayed on an electronic device such as a monitor or a tablet. In one or more examples, once the video data is received or in the process of being received (such as in real-time during the surgical procedure) the process 600 can move to step 606 wherein an indication can be received to capture an image from the received video.

In one or more examples, and as described in detail above, each template can include one or more pre-defined image slots corresponding to pre-defined annotations of the image slot. In one or more examples, the surgeon can capture images in a pre-defined order corresponding to the one or more pre-defined image slots. For instance, referring to the example of FIG. 7A, image slots 702, 706, and 710 can represent a pre-defined order in which the template 700 expects the images to be populated in the template to be received. Thus, during the surgery, the surgeon can know the order in which they need to take or select images for the report and can provide an indication at step 606 when they want to capture an image corresponding to a particular image slot of the template.

In one or more examples, the indication to capture an image can be received using a variety of methods. In one or more examples, the surgeon can push a button on the imaging tool itself indicating that they wish to capture an image at the precise moment the button is pushed. In one or more examples, the button can be elsewhere. For instance, rather than being on the imaging device itself, the button can take the form of a foot pedal, or other mechanical input device that is communicatively coupled to a processor that can capture image data from the received video data. In one or more examples, the surgeon using a tablet or other touch sensitive device, can simply tap the screen where the video data is being displayed in order to capture an image. In some variations, rather than capturing an image at the precise moment the indication is received, capturing an image may comprise selecting an image from within a neighborhood of images obtained around the moment that the indication is received, such as selecting the clearest image from within that neighborhood and/or the image with the highest likelihood of depicting the feature of the corresponding template annotation.

Once all of the images required for a given template have been captured at step 608, the process 600 can move to step 610 wherein the annotations are displayed. In one or more examples, the process of displaying the annotations can be substantially similar to the process described above with respect to step 312 of FIG. 3. Thus, as described above with respect to step 312 of FIG. 3, displaying annotations can, in one or more examples, include appending metadata to one or more images captured during a surgical procedure, and overlaying or placing the annotations next to an image on an electronic display, a printed report, or both.

In one or more examples of the disclosure, the images that populate a given image slot can be automatically populated into the template based on the video data acquired by the endoscopic imaging device. Referring back to FIG. 3, in one or more examples, image frames captured from received video data at step 304 can be processed using one or more machine classifiers at step 306 as described above. As described above, at step 308, characteristics associated with the image can be determined based on one or more classifier metrics. However, in one or more examples, rather than generating the annotations for the image, the identified characteristics can be checked against the image slot of a pre-defined template to see if there is a match and if the classified image matches one of the pre-defined image slots, then that image can be placed into the template at the matching slot.

FIG. 7B illustrates another exemplary annotation template according to examples of the disclosure. In one or more examples, a graphical user interface 714 can be presented to a surgeon or user of the system shown on an electronic display during a surgical procedure in which an endoscopic imaging device is being used to visualize a cavity in the internal area of a patient. In one or more examples, the graphical user interface 714 can include a video display area 716 that can display the video data being generated by the endoscopic imaging device in real time.

In one or more examples of the disclosure, the graphical user interface can include a template 718 that can be pre-selected by a surgeon prior to the surgical procedure. As illustrated in FIG. 7B, the template 718 can include one or more annotations 719 that define labels to be applied to images captured during the surgery. In contrast to the example of FIG. 7A, in the example of FIG. 7B, the images that populate the image slots associated with annotations 719 can be automatically selected by the system as described above. For instance, as shown in FIG. 7B the system can automatically detect when the video data 716 shows a medial meniscus repair using the methods and systems described above with respect to FIGS. 3-4. Once the system detects that an image captured from the video data matches one of the annotations 719, in one or more examples, the system can place the image in the image slot corresponding to that annotation.

In one or more examples, and as shown in FIG. 7B, once an image is associated with an annotation, the surgeon can be presented with the captured image as shown at 720. In one or more examples, the surgeon can be asked to confirm that the captured image selected by the system indeed corresponds to the annotation. In one or more examples, the surgeon can confirm that the captured and selected image 720 corresponds to the annotation 719 by pressing a button located on the endoscopic imaging device or by engaging with any other input mechanism that can allow for the system to receive input from the surgeon thus allowing the surgeon to confirm that the captured and selected image associated with a particular annotation is correct.

In one or more examples, in addition to selecting a captured image, the system can also identify a region 722 in the captured image in which the phenomenon associated with the image is precisely shown in the image. In one or more examples, the system can determine the metes and bounds of the region 722 using one or more Region Based Convolutional Neural Networks (RCNN) that is configured to not only identify images that contain certain characteristics, but can also identify one or more portions within the image where the characteristic is found.

In one or more examples, the template can be flexible to match the video data acquired by the endoscopic imaging device. For instance, a surgeon may pre-select a template, however if the system is able to classify one or more images captured by the endoscopic imaging device as containing a characteristic not addressed by the pre-selected annotations from a template, the system may suggest to the surgeon to add an image to the template with the appropriate annotation corresponding to the characteristic. In one or more examples, the process of confirming additions to the template or confirming images to be associated with the template annotations can occur during the surgical procedure, or can be performed post-surgery.

Figure 8A:
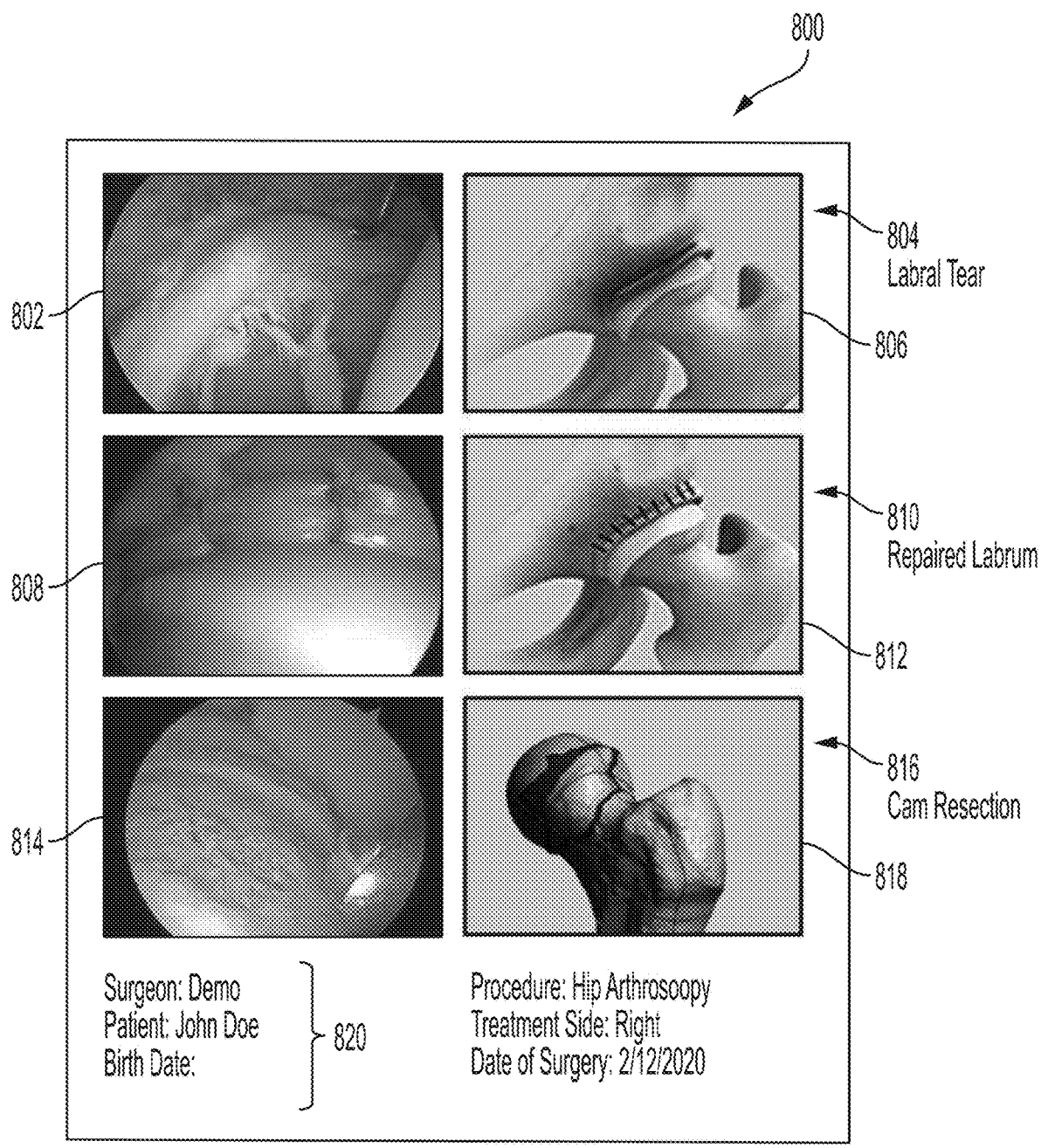
FIG. 8A and FIG. 8B illustrate exemplary images annotated according to the examples provided herein according to examples of the disclosure.
Figure 8B:
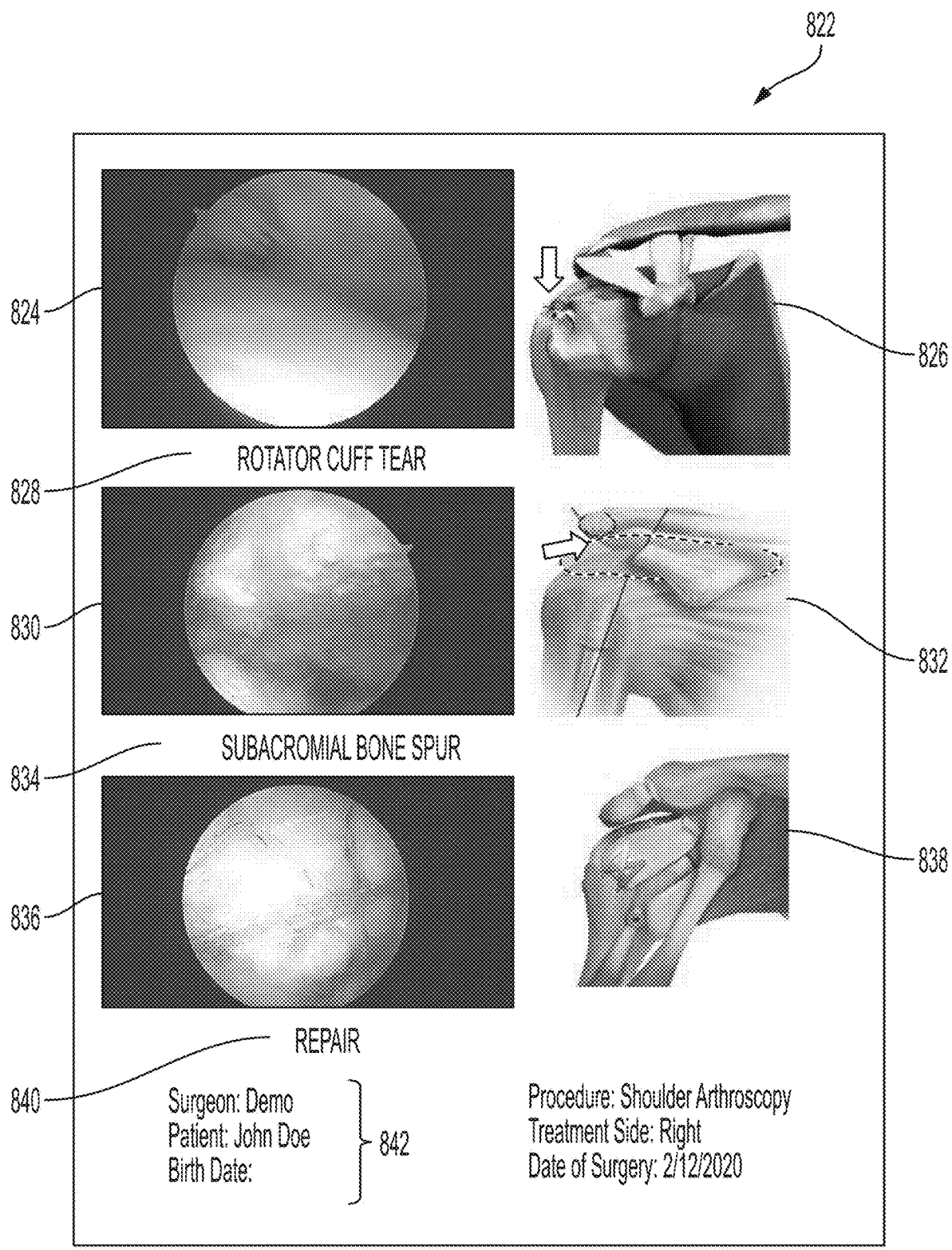

FIG. 8A and FIG. 8B illustrate exemplary annotated images according to examples of the disclosure. The examples of FIG. 8 provide an example in which the images captured during a surgical procedure are displayed on an electronic display or a printed report as described above with respect to step 610 of FIG. 6 and step 312 of FIG. 3. Furthermore, the annotated images shown in FIG. 8A and FIG. 8B can represent the product of either of the processes described above with respect to FIGS. 3 and 6. FIG. 8A illustrates a first exemplary annotation surgical report 800 according to examples of the disclosure.

In one or more examples, the report 800 can include a first image 802 captured during a surgical procedure according to the examples described above with respect to FIGS. 3 and 6. In accordance with the examples described above, two separate annotations 804 and 806 can be automatically applied to the image 802 and laid out on the report 800. The first annotation 806 is a graphic that provides the patient with the context for what 802 shows. In the example of image 802, the first annotation 806 can show a graphic of a hip joint with a labral tear, allowing the patient to thus understand that image 802 is of a hip joint with a labral tear. In one or more examples, the first annotation 806 (i.e., the graphic) can be overlaid with a second annotation 804 that describes in text what the image (as well as the graphic) is showing. Thus, in the example of report 800, the second annotation 804 is a label with the text "labral tear" that is overlaid on the graphic 806 (i.e., the first annotation). In one or more examples, the first and second annotations 804 and 806 can be automatically placed next to the image 802 so to that the patient can understand that the two annotations are associated with the image 802 (rather than another image in the report).

In one or more examples, the report 800 can include a second image 808 captured during a surgical procedure according to the examples described above with respect to FIGS. 3 and 6. In accordance with the examples described above, two separate annotations 810 and 812 can be automatically applied to the image 808 and laid out on the report 800. The first annotation 812 is a graphic that provides the patient with the context for what image 808 shows. In the example of image 808, the first annotation 812 illustrates a graphic of a hip joint with a repaired labral tear, allowing the patient to thus understand that image 808 is of a hip joint with a labrum after it has been repaired. In one or more examples, the first annotation 812 (i.e., the graphic) can be overlaid with a second annotation 810 that describes in text what the image (as well as the graphic) is showing. Thus, in the example of report 800, the second annotation 810 is a label with the text "Repaired Labrum" that is overlaid on the graphic 812 (i.e., the first annotation). In one or more examples, the first and second annotations 812 and 810 associated with image 808 can be automatically placed next to the image 808 so to that the patient can understand that the two annotations are associated with the image 808 (rather than another image in the report).

In one or more examples, the report 800 can include a third image 814 captured during a surgical procedure according to the examples described above with respect to FIGS. 3 and 6. In accordance with the examples described above, two separate annotations 816 and 818 can be automatically applied to the image 814 and laid out on the report 800. The first annotation 818 is a graphic that provides the patient with the context for what image 814 shows. In the example of image 814, the first annotation 818 illustrates a graphic of a femur bone with a cam resection, allowing the patient to thus understand that image 814 is of a femur bone with a cam after it has been resected. In one or more examples, the first annotation 818 (i.e., the graphic) can be overlaid with a second annotation 816 that describes in text what the image (as well as the graphic) is showing. Thus, in the example of report 800, the second annotation 816 is a label with the text "Cam Resection" that is overlaid on the graphic 818 (i.e., the first annotation). In one or more examples, the first and second annotations 816 and 818 associated with image 814 can be automatically placed next to the image 814 so to that the patient can understand that the two annotations are associated with the image 814 (rather than another image in the report).

In one or more examples, the report 800 can also include one or more annotations 820 that provide information about the patient as well as information about the procedure performed on the patient. Annotations 820 may not be associated with a particular image in the report, but can provide identifying image about the report such as the patient's name, the surgeon's name, the patient's birth date, the type of procedure, which side of the body the procedure was performed on, as well as the date the procedure was performed. The above are meant as examples, and should not be seen as limiting. Annotations 820 can include any type of information that the surgeon or medical practitioner wishes to include in the report.

FIG. 8B illustrates another exemplary report according to examples of the disclosure. The exemplary report 822 can be similar to the report 800 of FIG. 8A, but as illustrated, may include different information that is laid out in a different manner than the report 800 of FIG. 8A. In one or more examples, the report 822 includes a first image 824 that has two annotations 826 and 828. Annotation 826, as illustrated in FIG. 8B, is a graphic that provides the user with a context for what the image 824 shows. As indicated in the sample report 822, image 824 shows a torn rotator cuff. Thus, the graphic of annotation 826 shows the entire shoulder with an arrow indicating the precise location of the rotator cuff (that is depicted in the graph as being damaged). The graphic of annotation 826, thus not only provides the patient with context for what joint is pictured in image 824, but also shows the precise location where the image is taken from. In one or more examples, the image 824 includes a second annotation 828 that provides a textual description of what is shown in the image 824. As illustrated, annotation 828 labels the image 824 as a "Rotator Cuff Tear." In contrast to the example of FIG. 8A, the textual annotation 828 is laid underneath the image 824 rather than as overlaid on the graphic 826, thus illustrating an alternative layout of the annotations generated by the systems and methods described above.

In one or more examples, the report 822 includes a second image 830 that has two annotations 832 and 834. Annotation 832, as illustrated in FIG. 8B, is a graphic that provides the user with a context for what the image 830 shows. As indicated in the sample report 822, image 830 shows a subacromial bone spur. Thus, the graphic of annotation 832 shows the entire shoulder with an arrow indicating the precise location of where the bone spur is located. The graphic of annotation 832, thus not only provides the patient with context for what joint is pictured in image 830, but also shows the precise location where the image is taken from. In one or more examples, the image 830 includes a second annotation 834 that provides a textual description of what is shown in image 830. As illustrated, annotation 834 labels the image 830 as a "Subacromomial Bone Spur.

In one or more examples, the report 822 includes a third image 836 that has two annotations 838 and 840. Annotation 838, as illustrated in FIG. 8B, is a graphic that provides the user with a context for what the image 836 shows. As indicated in the sample report 822, image 836 shows a repaired rotator cuff. Thus, the graphic of annotation 838 shows the entire shoulder with a depiction of a rotator cuff that has been repaired. In one or more examples, the image 836 includes a second annotation 840 that provides a textual description of what is shown in the image 836. As illustrated, annotation 840 labels the image 836 as "Repair." Additionally, and similar to the example of FIG. 8A (and more specifically annotation 820), the sample report 822 can include an additional annotation 842 that is not associated with any particular image and that is configured to provide additional information about the patient and the procedure that was performed on them.

Figure 9:
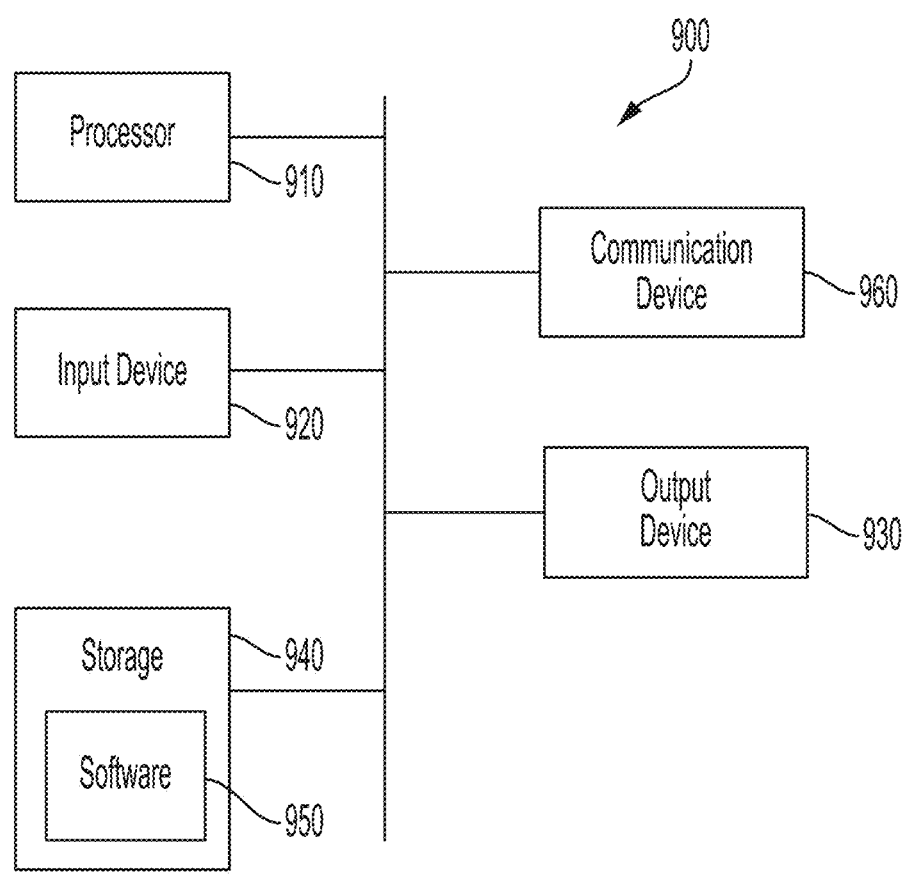
FIG. 9 illustrates an exemplary computing system, according to examples of the disclosure.

FIG. 9 illustrates an example of a computing system 900, in accordance with some examples of the disclosure that can be used for one or more of components of system 100 of FIG. 1, such as one or more of camera head 108, camera control unit 112, and image processing unit 116. System 900 can be a computer connected to a network, such as one or more networks of a hospital, including a local area network within a room of a medical facility and a network linking different portions of the medical facility. System 900 can be a client or a server. As shown in FIG. 9, system 900 can be any suitable type of processor-based system, such as a personal computer, workstation, server, handheld computing device (portable electronic device) such as a phone or tablet, or dedicated device. The system 900 can include, for example, one or more of input device 920, output device 930, one or more processors 910, storage 940, and communication device 960. Input device 920 and output device 930 can generally correspond to those described above and can either be connectable or integrated with the computer.

Input device 920 can be any suitable device that provides input, such as a touch screen, keyboard or keypad, mouse, gesture recognition component of a virtual/augmented reality system, or voice-recognition device. Output device 930 can be or include any suitable device that provides output, such as a display, touch screen, haptics device, virtual/augmented reality display, or speaker.

Storage 940 can be any suitable device that provides storage, such as an electrical, magnetic, or optical memory including a RAM, cache, hard drive, removable storage disk, or other non-transitory computer readable medium. Communication device 960 can include any suitable device capable of transmitting and receiving signals over a network, such as a network interface chip or device. The components of the computing system 900 can be connected in any suitable manner, such as via a physical bus or wirelessly.

Processor(s) 910 can be any suitable processor or combination of processors, including any of, or any combination of, a central processing unit (CPU), field programmable gate array (FPGA), and application-specific integrated circuit (ASIC). Software 950, which can be stored in storage 940 and executed by one or more processors 910, can include, for example, the programming that embodies the functionality or portions of the functionality of the present disclosure (e.g., as embodied in the devices as described above). For example, software 950 can include one or more programs for performing one or more of the steps of method 400, method 800, and/or method. 1000.

Software 950 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 940, that can contain or store programming for use by or in connection with an instruction execution system, apparatus, or device.

Software 950 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport computer readable medium can include, but is not limited to, an electronic, magnetic, optical, electromagnetic, or infrared wired or wireless propagation medium.

System 900 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

System 900 can implement any operating system suitable for operating on the network. Software 950 can be written in any suitable programming language, such as C, C++, Java, or Python. In various examples of the disclosure, application software embodying the functionality of the present disclosure can be deployed in different configurations, such as in a client/server arrangement or through a Web browser as a Web-based application or Web service, for example.

The foregoing description, for the purpose of explanation, has been described with reference to specific examples of the disclosure. However, the illustrative discussions above are not intended to be exhaustive or to limit the invention to the precise forms disclosed. Many modifications and variations are possible in view of the above teachings. The examples of the disclosure were chosen and described in order to best explain the principles of the techniques and their practical applications. Others skilled in the art are thereby enabled to best utilize the techniques and various examples of the disclosure with various modifications as are suited to the particular use contemplated. For the purpose of clarity and a concise description, features are described herein as part of the same or separate examples of the disclosure; however, it will be appreciated that the scope of the disclosure includes examples of the disclosure having combinations of all or some of the features described.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

The invention claimed is:

1. A method for annotating one or more images generated during a surgical procedure to provide additional information to a viewer of the images, the method comprising:
   receiving a selection of a pre-defined template for a report corresponding to the surgical procedure;
   receiving video data captured from an imaging tool configured to image an internal portion of a patient;
   extracting one or more image frames from the received video data;
   applying one or more machine learning classifiers to the received video data to generate one or more classification metrics based on the received video data, wherein the one or more machine learning classifiers are created using a supervised training process that comprises using one or more annotated images to train the machine learning classifier, wherein the one or more machine learning classifiers comprise a joint type machine learning classifier configured to generate one or more classification metrics associated with identifying a type of joint pictured in the received video data;
   identifying one or more characteristics in the one or more image frames based on the generated one or more classification metrics;
   determining that the one or more image frames correspond to one or more annotations that provide additional information to a viewer of the one or more image frames based on the identified one or more characteristics; and
   inserting the one or more image frames into the pre-defined template in association with the one or more annotations.

2. The method of claim 1, wherein the supervised training process comprises:
   applying one or more identifiers to each image of a plurality of images to indicate one or more characteristics associated with the image; and
   processing each image of the plurality of images and its corresponding one or more identifiers.

3. The method of claim 1, wherein the joint type machine learning classifier is configured to identify joints selected from the group consisting of a hip, a shoulder, and a knee.

4. The method of claim 1, wherein the one or more machine learning classifiers include a procedure stage machine learning classifier configured to generate one or more classification metrics associated with identifying a procedure stage being performed in the received video data.

5. The method of claim 1, wherein the one or more machine learning classifiers include an image clarity machine learning classifier configured to generate one or more classification metrics associated with a clarity of the received video data.

6. The method of claim 5, wherein the image clarity machine classifier is configured to generate one or more classification metrics associated with an amount of blood visible in the received video data.

7. The method of claim 5, wherein the image clarity machine classifier is configured to generate one or more classification metrics associated with an amount of bubbles visible in the received video data.

8. The method of claim 5, wherein the image clarity machine classifier is configured to generate one or more classification metrics associated with an amount of debris visible in the received video data.

9. A system for annotating one or more images generated during a surgical procedure to provide additional information to a viewer of the images, the system comprising:
a memory;
one or more processors;
wherein the memory stores one or more programs that when executed by the one or more processors, cause the one or more processors to:
receive a selection of a pre-defined template for a report corresponding to a surgical procedure;
receive video data captured from an imaging tool configured to image an internal portion of a patient;
extract one or more image frames from the received video data;
apply one or more machine learning classifiers to the received video data to generate one or more classification metrics based on the received video data, wherein the one or more machine learning classifiers are created using a supervised training process that comprises using one or more annotated images to train the machine learning classifier, wherein the one or more machine learning classifiers comprise a joint type machine learning classifier configured to generate one or more classification metrics associated with identifying a type of joint pictured in the received video data;
identify one or more characteristics in the one or more image frames based on the generated one or more classification metrics;
determine that the one or more image frames correspond to one or more annotations that provide additional information to a viewer of the one or more image frames based on the identified one or more characteristics; and
insert the one or more image frames into the pre-defined template in association with the one or more annotations.

10. The system of claim 9, wherein the supervised training process comprises:
applying one or more identifiers to each image of a plurality of images to indicate one or more characteristics associated with the image; and
processing each image of the plurality of images and its corresponding one or more identifiers.

11. The system of claim 9, wherein the joint type machine learning classifier is configured to identify joints selected from the group consisting of a hip, a shoulder, and a knee.

12. The system of claim 9, wherein the one or more machine learning classifiers include a procedure stage machine learning classifier configured to generate one or more classification metrics associated with identifying a procedure stage being performed in the received video data.

13. The system of claim 9, wherein the one or more machine learning classifiers include an image clarity machine learning classifier configured to generate one or more classification metrics associated with a clarity of the received video data.

14. The system of claim 13, wherein the image clarity machine classifier is configured to generate one or more classification metrics associated with an amount of blood visible in the received video data.

15. The system of claim 13, wherein the image clarity machine classifier is configured to generate one or more classification metrics associated with an amount of bubbles visible in the received video data.

16. The system of claim 13, wherein the image clarity machine classifier is configured to generate one or more classification metrics associated with an amount of debris visible in the received video data.

17. A non-transitory computer readable storage medium storing one or more programs for execution by one or more processors of an electronic device that when executed by the device, cause the device to:
receive a selection of a pre-defined template for a report corresponding to the surgical procedure;
receive video data captured from an imaging tool configured to image an internal portion of a patient;
extract one or more image frames from the received video data;
apply one or more machine learning classifiers to the received video data to generate one or more classification metrics based on the received video data, wherein the one or more machine learning classifiers are created using a supervised training process that comprises using one or more annotated images to train the machine learning classifier, wherein the one or more machine learning classifiers comprise a joint type machine learning classifier configured to generate one or more classification metrics associated with identifying a type of joint pictured in the received video data;
identify one or more characteristics in the one or more image frames based on the generated one or more classification metrics;
determine that the one or more image frames correspond to one or more annotations that provide additional information to a viewer of the one or more image frames based on the identified one or more characteristics; and
insert the one or more image frames into the pre-defined template in association with the one or more annotations.

18. The non-transitory computer readable storage medium of claim 17, wherein the supervised training process comprises:
applying one or more identifiers to each image of a plurality of images to indicate one or more characteristics associated with the image; and
processing each image of the plurality of images and its corresponding one or more identifiers.

19. The non-transitory computer readable storage medium of claim 17, wherein the joint type machine learning classifier is configured to identify joints selected from the group consisting of a hip, a shoulder, and a knee.

20. The non-transitory computer readable storage medium of claim 17, wherein the one or more machine learning classifiers include a procedure stage machine learning classifier configured to generate one or more classification metrics associated with identifying a procedure stage being performed in the received video data.

21. The non-transitory computer readable storage medium of claim 17, wherein the one or more machine learning classifiers include an image clarity machine learning classifier configured to generate one or more classification metrics associated with a clarity of the received video data.

22. The non-transitory computer readable storage medium of claim 21, wherein the image clarity machine classifier is configured to generate one or more classification metrics associated with an amount of blood visible in the received video data.

23. The non-transitory computer readable storage medium of claim 21, wherein the image clarity machine classifier is configured to generate one or more classification metrics associated with an amount of bubbles visible in the received video data.

24. The non-transitory computer readable storage medium of claim 21, wherein the image clarity machine classifier is configured to generate one or more classification metrics associated with an amount of debris visible in the received video data.

\* \* \* \* \*